US00PP20220P2

(12) United States Plant Patent
Mii et al.

(10) Patent No.: US PP20,220 P2
(45) Date of Patent: Aug. 18, 2009

(54) ***PRIMULA* PLANT NAMED 'THIRTYONE'**

(50) Latin Name: ***Primula filchnera*×*Primula sinensis***
Varietal Denomination: Thirtyone

(75) Inventors: Masahiro Mii, Tokyo (JP); Junji Amano, Aichi (JP); Juntaro Kato, Aichi (JP)

(73) Assignee: Doc Co. Ltd., Tokyo (JP)

( * ) Notice: Subject to any disclaimer, the term of this patent is extended or adjusted under 35 U.S.C. 154(b) by 293 days.

(21) Appl. No.: 11/731,868

(22) Filed: Mar. 30, 2007

(51) Int. Cl.
*A01H 5/00* (2006.01)

(52) U.S. Cl. ..... Plt./472

(58) Field of Classification Search ..... Plt./472, Plt./263.1

See application file for complete search history.

*Primary Examiner*—Howard J Locker
(74) *Attorney, Agent, or Firm*—C. A. Whealy

(57) ABSTRACT

A new and distinct cultivar of *Primula* plant named 'Thirtyone', characterized by its upright plant habit; vigorous growth habit; freely flowering habit; and light purple-colored flowers that are held above and beyond the foliage on strong peduncles.

2 Drawing Sheets

Botanical designation: *Primula filchnera*×*Primula sinensis.*
Cultivar denomination: 'Thirtyone'.

BACKGROUND OF THE INVENTION

The present invention relates to a new and distinct cultivar of *Primula,* botanically known as *Primula filchnera*× *Primula sinensis,* and hereinafter referred to by the name 'Thirtyone'.

The new *Primula* is a product of a planned breeding program conducted by the Inventors in Chiba, Japan. The objective of the breeding program is to create new vigorous *Primula* cultivars with strong growth and early flowering habits.

The new *Primula* originated from a cross-pollination made by the Inventors in April, 2002 in Chiba, Japan of an unnamed proprietary selection of *Primula filchnera,* not patented, as the female, or seed, parent with an unnamed proprietary selection of *Primula sinensis,* not patented, as the male, or pollen, parent. The new *Primula* was discovered and selected by the Inventors as a single flowering plant within the progeny of the stated cross-pollination in a controlled environment in Chiba, Japan in August, 2002.

Asexual reproduction of the new *Primula* by micropropagation in a controlled environment in Chiba, Japan since October, 2002 has shown that the unique features of this new *Primula* are stable and reproduced true to type in successive generations.

SUMMARY OF THE INVENTION

The cultivar Thirtyone has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Thirtyone'. These characteristics in combination distinguish 'Thirtyone' as a new and distinct cultivar of *Primula:*

1. Upright plant habit.
2. Vigorous growth habit.
3. Freely flowering habit.
4. Light purple-colored flowers that are held above and beyond the foliage on strong peduncles.

Plants of the new *Primula* can be compared to plants of the female parent selection. Plants of the new *Primula* differ from plants of the female parent selection in the following characteristics:

1. Leaves of plants of the new *Primula* have less deeply incised margins than leaves of plants of the female parent selection.
2. Flowers of the new *Primula* and the female parent selection differ in flowers color.
3. Plants of the new *Primula* are more high temperature tolerant than plants of the female parent selection.

Plants of the new *Primula* can be compared to plants of the male parent selection. Plants of the new *Primula* differ from plants of the male parent selection in the following characteristics:

1. Leaves of plants of the new *Primula* have more deeply incised margins than leaves of plants of the male parent selection.
2. Plants of the new *Primula* are more freely flowering than plants of the male parent selection.
3. Plants of the new *Primula* and the male parent selection differ in flower color.

Plants of the new *Primula* can be compared to plants of the *Primula sinensis* cultivar Fanfare, not patented. In side-by-side comparisons conducted in Chiba, Japan, plants of the new *Primula* differed from plants of the cultivar Fanfare in the following characteristics:

1. Plants of the new *Primula* were taller than plants of the cultivar Fanfare.
2. Leaves of plants of the new *Primula* were larger than leaves of plants of the cultivar Fanfare.

3. Flowers of plants of the new *Primula* were larger than flowers of plants of the cultivar Fanfare.
4. Plants of the new *Primula* and the cultivar Fanfare differed in petal color as plants of the cultivar Fanfare had white-colored petals.
5. Plants of the new *Primula* and the cultivar Fanfare differed in sepal color as plants of the cultivar Fanfare had red purple-colored sepals.
6. Plants of the new *Primula* had longer and thicker peduncles than plants of the cultivar Fanfare,

BRIEF DESCRIPTION OF THE PHOTOGRAPHS

The accompanying colored photographs illustrate the overall appearance of the new *Primula,* showing the colors as true as it is reasonably possible to obtain in colored reproductions of this type. Colors in the photographs may differ slightly from the color values cited in the detailed botanical description which accurately describe the colors of the new *Primula.*

The photograph on the first sheet comprises a side perspective view of a typical flowering plant of 'Thirtyone' grown in a container.

The photograph on the second sheet is a close-up view of typical flowers of 'Thirtyone'.

DETAILED BOTANICAL DESCRIPTION

The aforementioned photographs and following observations, measurements and values describe plants grown in Tokyo, Japan in 15-cm containers in a glass-covered greenhouse during the winter and under conditions which closely approximate commercial production. During the production of the plants, day temperatures ranged from 10° C. to 35° C., night temperatures ranged from 0° C. to 20° C. and light levels averaged 50 kilolux. Plants were about six months old when the photographs and the description were taken. In the description, color references are made to The Royal Horticultural Society Colour Chart, 2001 Edition, except where general terms of ordinary dictionary significance are used.

Botanical classification: *Primula filchnera*×*Primula sinensis* cultivar Thirtyone.

Parentage:

*Female, or seed, parent.*—Unnamed proprietary selection of *Primula filchnera,* not patented.

*Male, or pollen, parent.*—Unnamed proprietary selection of *Primula sinensis,* not patented.

Propagation:

*Type.*—By tissue culture.

*Time to initiate roots.*—About three weeks at 18° C. to 25° C.

*Time to produce a rooted cutting.*—About five to six weeks at 18° C. to 25° C.

*Root description.*—Fibrous; white and red purple in color.

*Rooting habit.*—Moderately freely branching; moderately dense.

Plant description:

*Plant habit.*—Upright and uniform plant habit; inverted triangle. Vigorous growth habit. Freely basal branching; about ten to twelve branches develop per plant.

*Plant height.*—About 21 cm.

*Plant width* (*spread*).—About 25 cm to 30 cm.

Foliage description:

*Arrangement.*—Basal, simple.

*Length.*—About 14 cm.

*Width.*—About 13 cm.

*Shape.*—Roughly cordate.

*Apex.*—Obtuse.

*Base.*—Acute.

*Margin.*—Crenate.

*Texture, upper and lower surfaces.*—Pubescent; rugose.

*Venation pattern.*—Pinnate.

*Color.*—Developing and fully expanded leaves, upper surface: 137B; venation, 144A, towards the base, 60A. Developing and fully expanded leaves, lower surface: 139C; towards the base, 61A; venation: 143C, towards the base, 60A.

*Petiole length.*—About 13 cm.

*Petiole diameter.*—About 7 mm.

*Petiole texture, upper and lower surfaces.*—Pubescent.

*Petiole color, upper and lower surfaces.*—60A.

Flower description:

*Flower type/habit.*—Single rounded and salverform flowers arranged on umbels on upright and strong peduncles; flowers face mostly upright. Freely flowering habit with about 5 to 15 flowers per umbel.

*Fragrance.*—Fragrant, not pleasant; typical of species.

*Natural flowering season.*—Flowering occurs naturally during the spring in Japan. Flowers last about one to two weeks on the plant; flowers not persistent.

*Flower buds.*—Height: About 1.2 cm to 1.7 cm. Diameter: About 4 to 5 mm. Shape: Elliptic. Color: Between 144A and 200A.

*Inflorescence height.*—About 4 cm to 10 cm.

*Inflorescence width.*—About 5 cm to 12 cm.

*Flower diameter.*—About 4 cm.

*Flower depth.*—About 2 cm.

*Petals.*—Quantity per flower: About five in a single whorl. Length (including tube): About 1.5 cm. Width: About 1.1 cm to 1.4 cm. Shape: Obcordate. Apex: Shallowly emarginate. Margin: Finely crenate. Texture, upper and lower surfaces: Smooth, glabrous. Color: Developing petals, upper and lower surfaces: Towards the margins, N80A; towards the center, N80B; at the center, 155B. Fully expanded petals, upper surface: Towards the margins, N80A to N80B; towards the center, 77C to 77D to N155B; at the center, N144A. Fully expanded petals, lower surface: Towards the margins, N80A; towards the center, 77DB; at the center, N155B.

*Sepals.*—Quantity per flower: Typically five fused in a single whorl. Length: About 1 cm to 1.5 cm. Width: About 0.8 cm to 1.2 cm. Shape: Lanceolate. Apex: Acute. Margin: Serrate. Texture, upper surface: Smooth, glabrous. Texture, lower surface: Pubescent. Color, upper and lower surfaces: Between 144A and 200A.

*Peduncles.*—Length: About 15 cm to 21 cm. Diameter: About 6 mm. Orientation: Mostly erect. Strength: Strong. Texture: Pubescent; rough. Color: 178A.

*Pedicels.*—Length: About 2 cm to 5 cm. Diameter: About 1.5 mm. Orientation: Outward. Strength: Moderately strong. Texture: Pubescent. Color: Between 148B and 178A.

*Reproductive organs.*—Stamens: Quantity/arrangement: Four per flower. Anther shape: Oblong. Anther length: About 2 mm. Anther color: 2C. Pollen amount: None observed. Pistils: Quantity: One per flower. Pistil length: About 1 cm. Stigma shape: Dome-like. Stigma color: 149A. Style length: About 5 mm. Style color: 149D. Ovary color: 144C. Fruits/seed: Fruit and seed development have not been observed.

Garden performance: Plants of the new *Primula* have been observed to tolerate wind, rain and temperatures from about −5° C. to about 40° C.

Pathogen/pest resistance: Plants of the new *Primula* have not been observed to be resistant to pathogens and pests common to *Primulas*.

It is claimed:

1. A new and distinct *Primula* plant named 'Thirtyone' as illustrated and described.

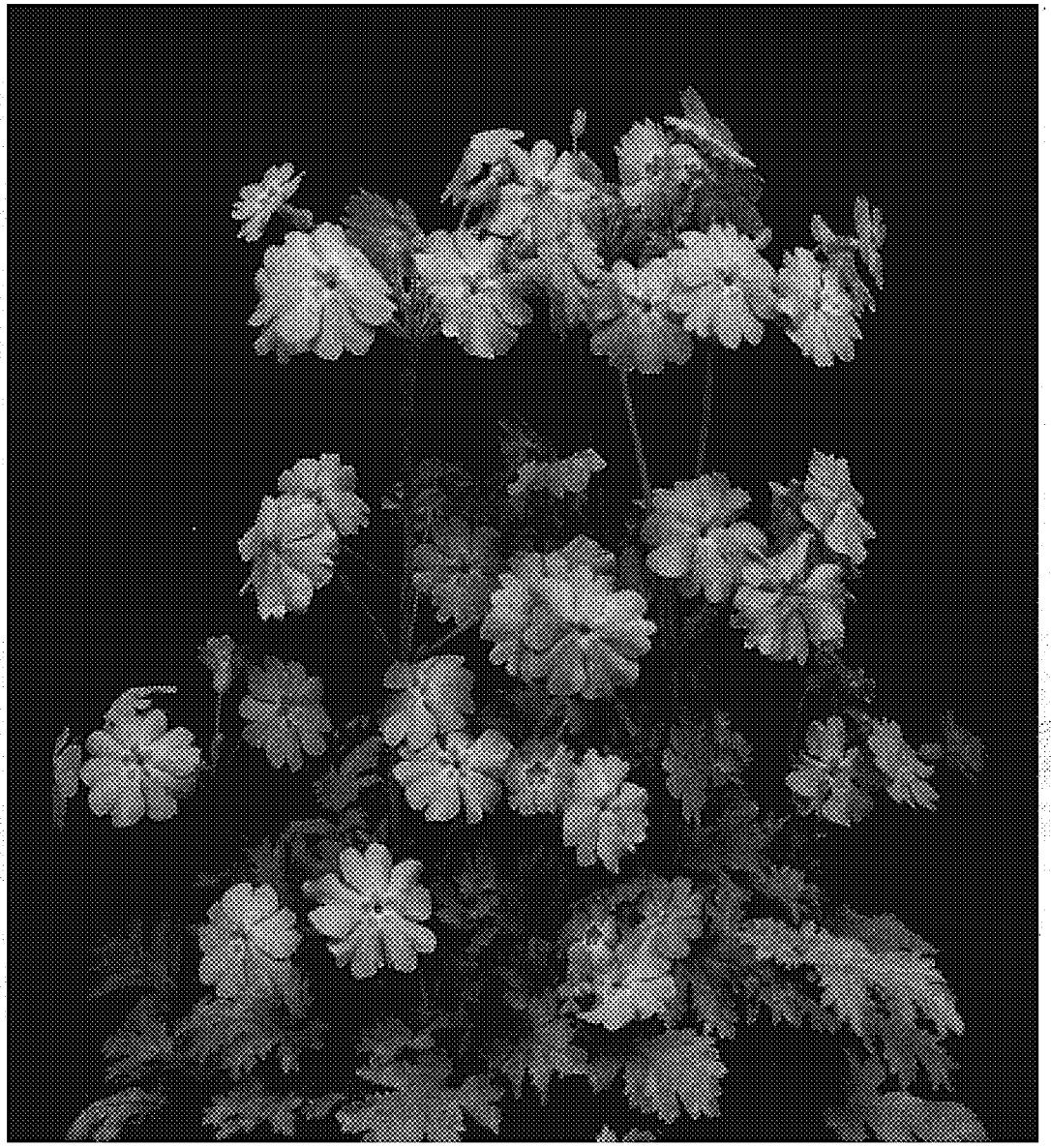

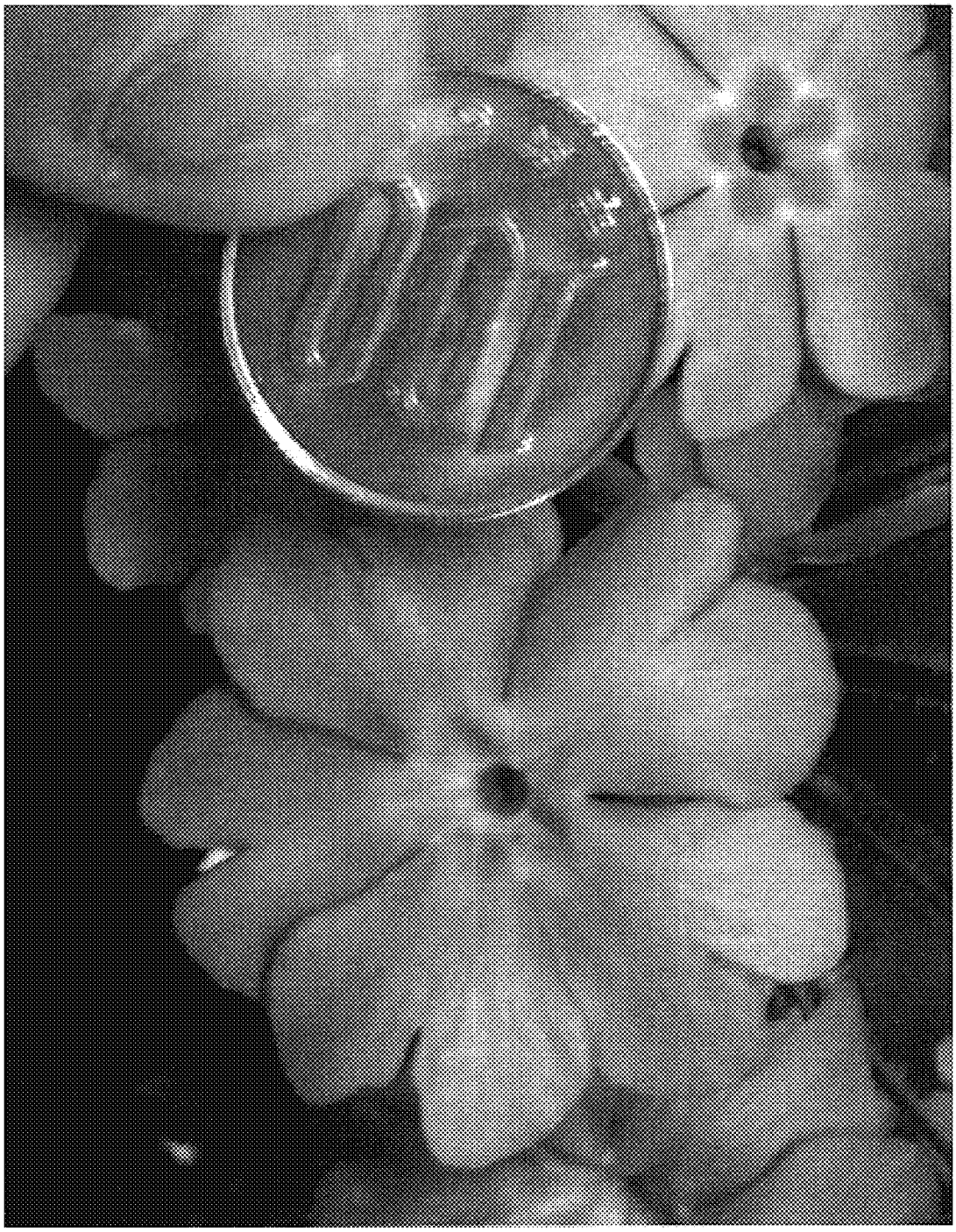

* * * * *